(12) United States Patent
Villa et al.

(10) Patent No.: US 8,932,051 B1
(45) Date of Patent: Jan. 13, 2015

(54) DENTAL PROSTHESIS FOR CATTLE AND METHOD FOR MOUNTING IT

(71) Applicants: Alfredo Villa, Ciudad Mendoza (AR); Pablo Granella, Ciudad Mendoza (AR)

(72) Inventors: Alfredo Villa, Ciudad Mendoza (AR); Pablo Granella, Ciudad Mendoza (AR)

(*) Notice: Subject to any disclaimer, the term of this patent is extended or adjusted under 35 U.S.C. 154(b) by 0 days.

(21) Appl. No.: 13/858,590

(22) Filed: Apr. 8, 2013

(51) Int. Cl.
*A61D 5/00* (2006.01)

(52) U.S. Cl.
CPC .................................. *A61D 5/00* (2013.01)
USPC ............................................................ 433/1

(58) Field of Classification Search
USPC .............................................. 433/1, 167–176
See application file for complete search history.

(56) References Cited

U.S. PATENT DOCUMENTS 3,140,543 A * 7/1964 Menter .............................. 433/1
3,462,838 A * 8/1969 Alstergren ........................ 433/1
5,073,111 A * 12/1991 Daftary ......................... 433/173
5,362,235 A * 11/1994 Daftary ......................... 433/172
6,196,838 B1   3/2001 Lukase et al.

* cited by examiner

*Primary Examiner* — Sunil K Singh
(74) *Attorney, Agent, or Firm* — Jesus Sanchelima, Esq.; Christian Sanchelima, Esq.; Sanchelima & Associates, P.A.

(57) ABSTRACT

A dental prosthesis for cattle, and method for mounting it, that includes mounting fastening members in the animals incisor, away from the central nerve and towards in the inner side of the incisor. Tying the incisors individually with surgical wire and to a support plate with through holes to immobilize the relative movement of the incisor with respect to each other. A malleable metallic overdenture is then mounted over the teeth and metallic infrastructure conforming to the incisors to define a conforming overdenture. An adhesive bonding agent is used to mount the overdenture to the incisors and the anchorage structure with retention fastening members that transversally pass through the overdenture and between the incisors to further secure the overdenture to the cured boding agent.

1 Claim, 6 Drawing Sheets

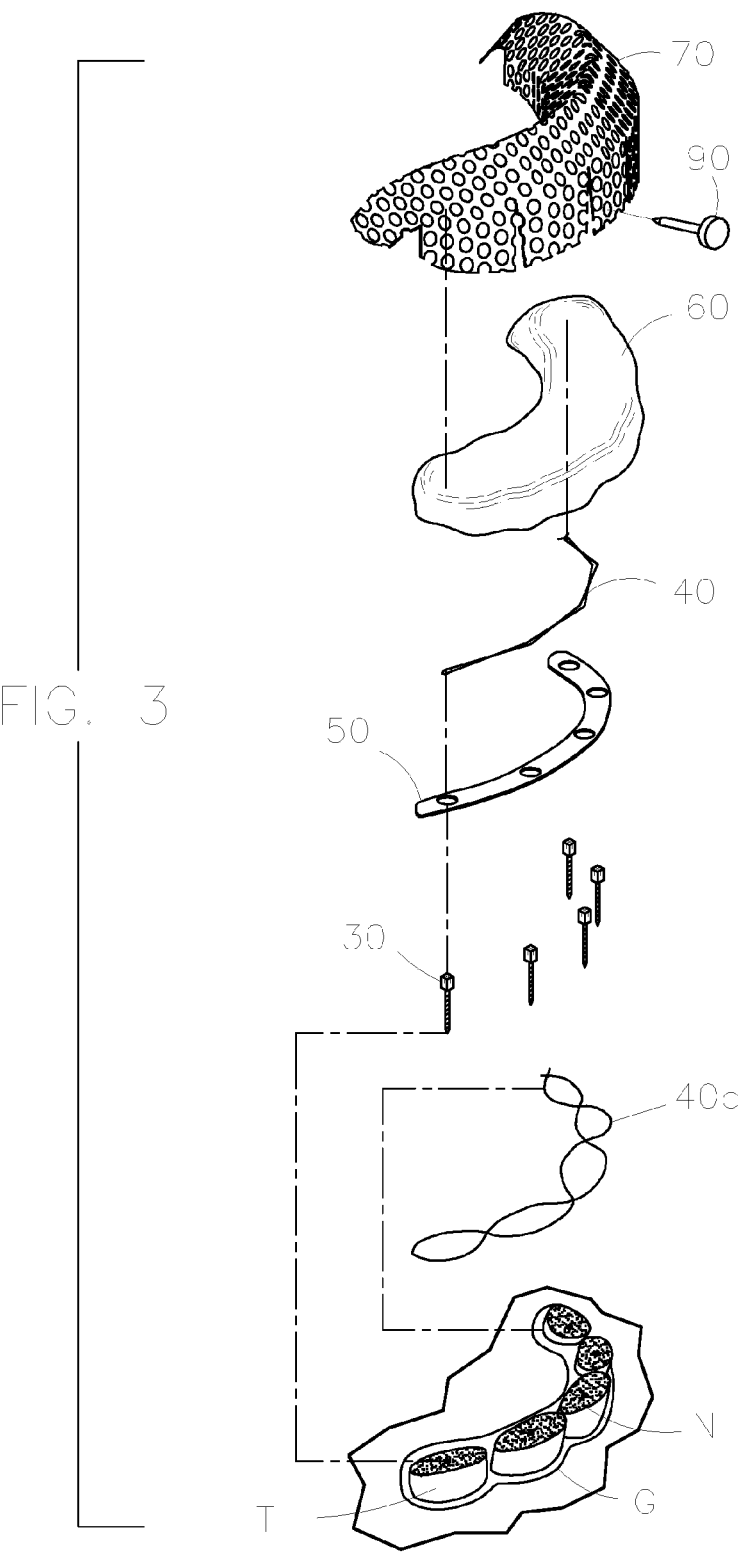

DENTAL PROSTHESIS FOR CATTLE AND METHOD FOR MOUNTING IT

BACKGROUND OF THE INVENTION

1. Field of the Invention

The present invention relates to a dental prosthesis and method for mounting same on the anterior incisors of cattle.

2. Description of the Related Art

Several designs for bovine dental crown devices have been designed in the past. None of them, however, include a metallic overdenture prosthesis that is fastened to the anterior incisors, as a group, to prevent individual movement of the teeth but substantially preserves the natural movement of the animal's mastication process. The bonding action of resins is enhanced with a mechanical fastening infrastructure with strategically located anchorage into and by (between) the animals teeth to ensure the long-term operability of the dental prosthesis.

The problem with wear and tear of bovine teeth has been widely documented. In particular the incisors (front teeth) wear out by the animal's constant mastication resulting in incisors defining a worn out plane that approaches its gum. Eventually, the animal cannot feed itself and perishes prematurely. Many attempts to solve the problem have achieved partial and temporary success, at most. For a description of the problem in this field, one of the related references succinctly summarizes it. See U.S. Pat. No. 6,196,838 (Lukase) at Col. 1, lines 10-50. Lukase's overdenture procedure and device, as others before him, uses a polymer with additives that bond to the mandibular teeth. However, the bonds wear off in relatively short periods of time, if they do not fall off before they wear out also. As in Lukase's patent, the present invention immobilizes all the teeth, as a group. However, the present invention also uses a metal ferrule and an overdenture prosthesis (made out of semi-malleable steel or other hard malleable metal) is bonded to interconnected anchorage screws mounted on the animal's teeth themselves. And the teeth are tied with wire to immobilize them and not merely rely on the bonding resin customarily used. Lastly, transversal fastening members are used to enhance the engagement provided by the bonding resin, which inevitably loosens with the stress/relaxation action of normal and continuous mastication. These novel and none obvious structural features make the present prosthesis superior to Lakase's patent and other references in the state of the art.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a prosthesis and procedure for mounting it in a cow's incisors that remains mounted and operational for an indefinite time period.

It is another object of this invention to provide a prosthesis and procedure that can be implemented with minimum pain for the animal permitting the animal to start eating immediately after the procedure.

It is yet another object of this invention to provide such a prosthesis that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1C is similar to the previous two figures showing one of the patterns used for wire 40a.

FIG. 3 illustrates an exploded view with teeth T shown in the previous figure at the bottom and the different elements to be subsequently mounted, including optional wire 40A, screws 30, elongated bracing plate 50 to immobilize teeth T with respect to each other, wire 40, bonding agent 60 and malleable metal overdenture 70.

DETAILED DESCRIPTION OF THE EMBODIMENTS OF THE INVENTION

Figure 1:
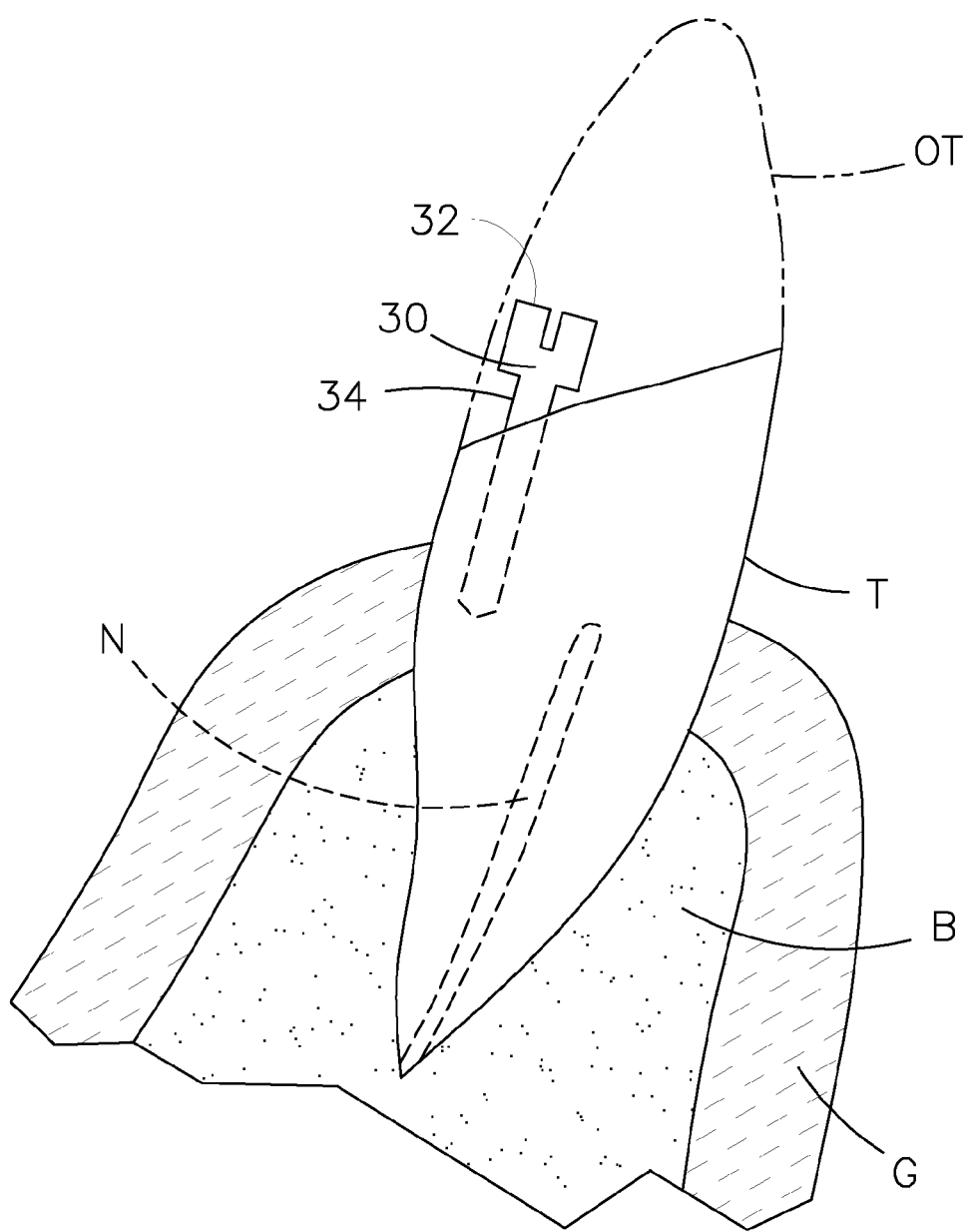
FIG. 1 represents an elevational view of a worn off incisor tooth T with the original tooth (OT) shape represented in broken lines.
Figure 1A:
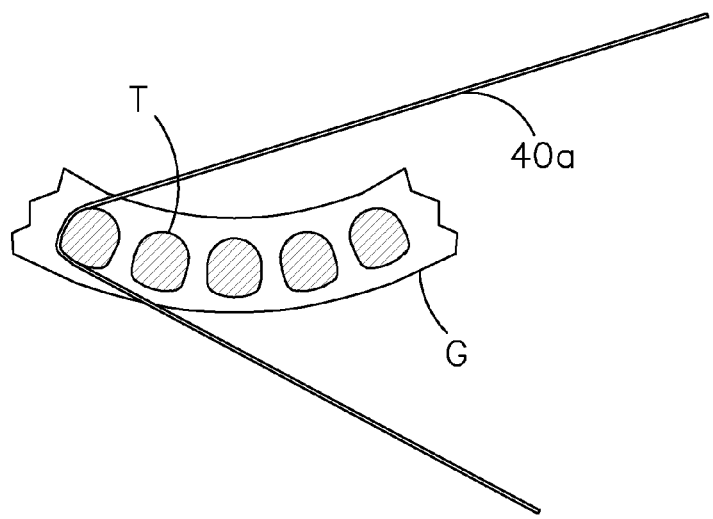
FIG. 1A shows a top view of a cow's anterior incisors with one of the ends' tooth being tied. This step is optional and applied at the discretion of the user or veterinarian using wire 40A.
Figure 1B:
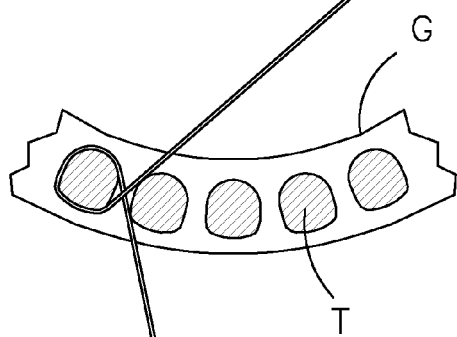
FIG. 1B is similar to the previous figure showing the adjacent tooth tied.
Figure 1C:
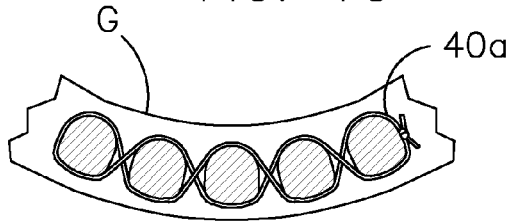
Figure 2:
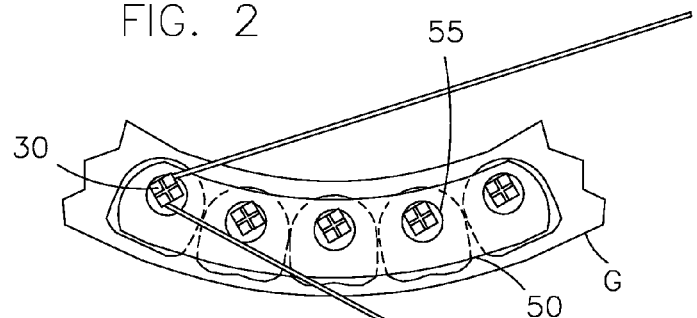
FIG. 2 shows a top view of a cow's anterior incisors with anchorage screws 30 mounted thereon, off centered to avoid the central nerve N, with one of the ends' tooth's screw 30 being tied with a wire.
Figure 2A:
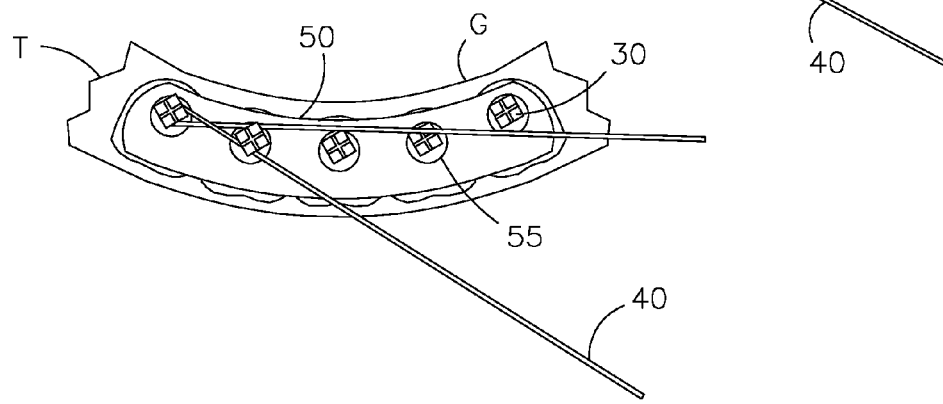
FIG. 2A is similar to the previous figure showing the adjacent tooth being tied.
Figure 2B:
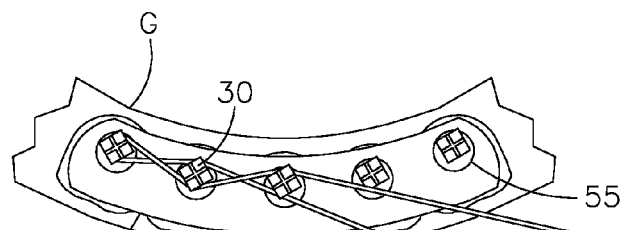
FIG. 2B is similar to the previous figures showing how a number-8 configuration of the wire.
Figure 2C:
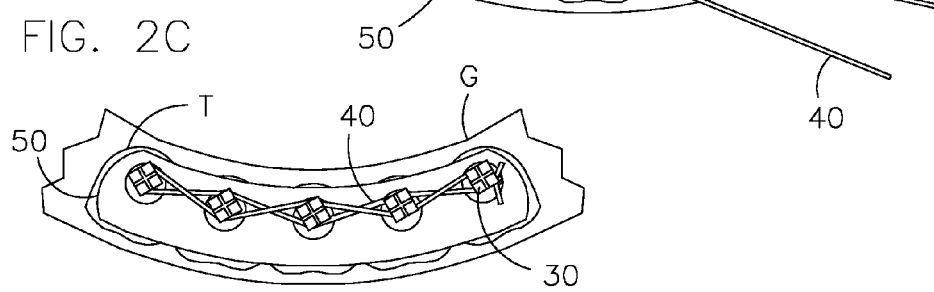
FIG. 2C shows an embodiment for tying screws 30 of the animals' incisors.
Figure 4:
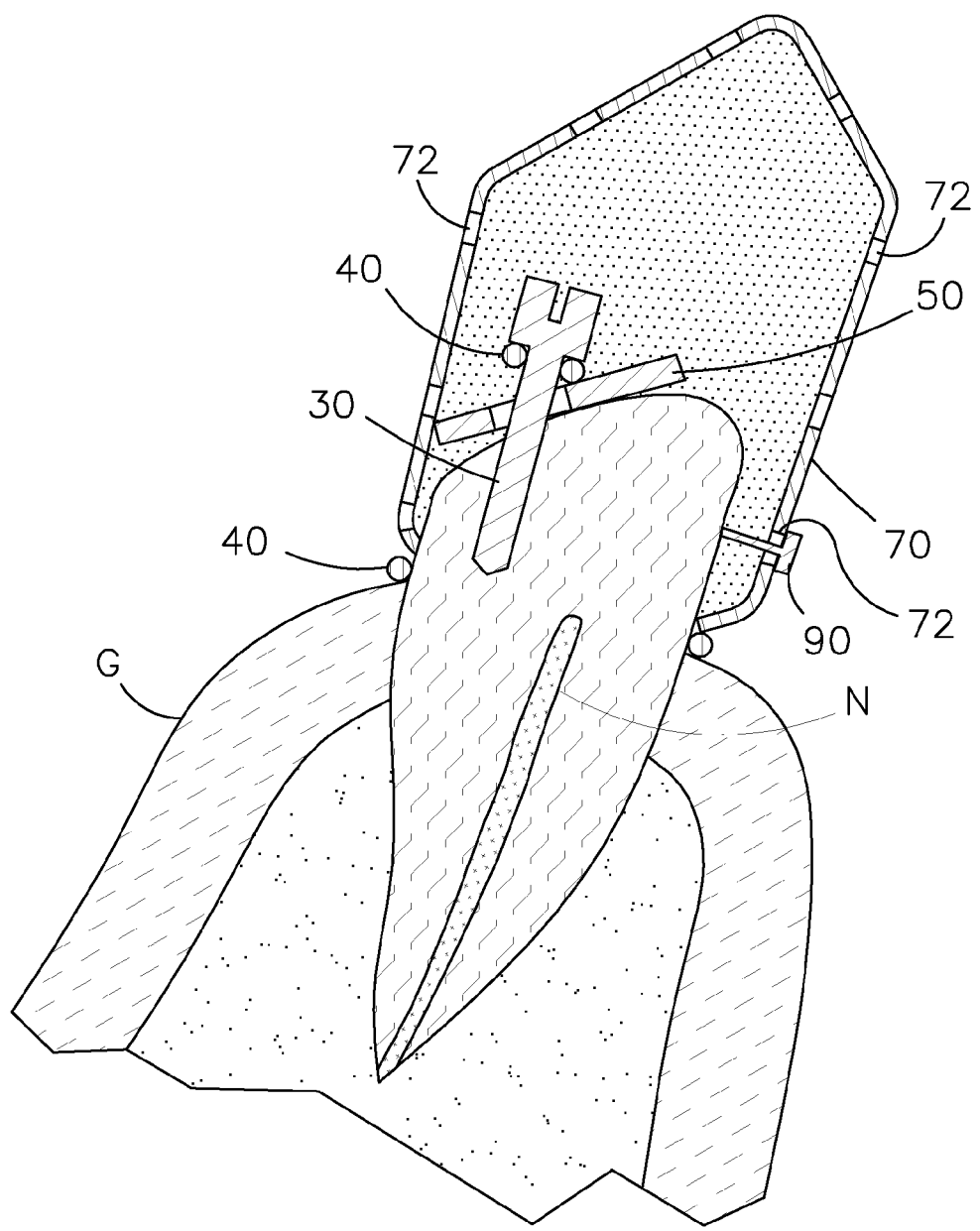
FIG. 4 is a cross-sectional representation of tooth T shown in FIG. 1 with the metallic prosthesis mounted thereon over a resin-bonding compound and further illustrating the disposition of the other elements.
Figure 5:
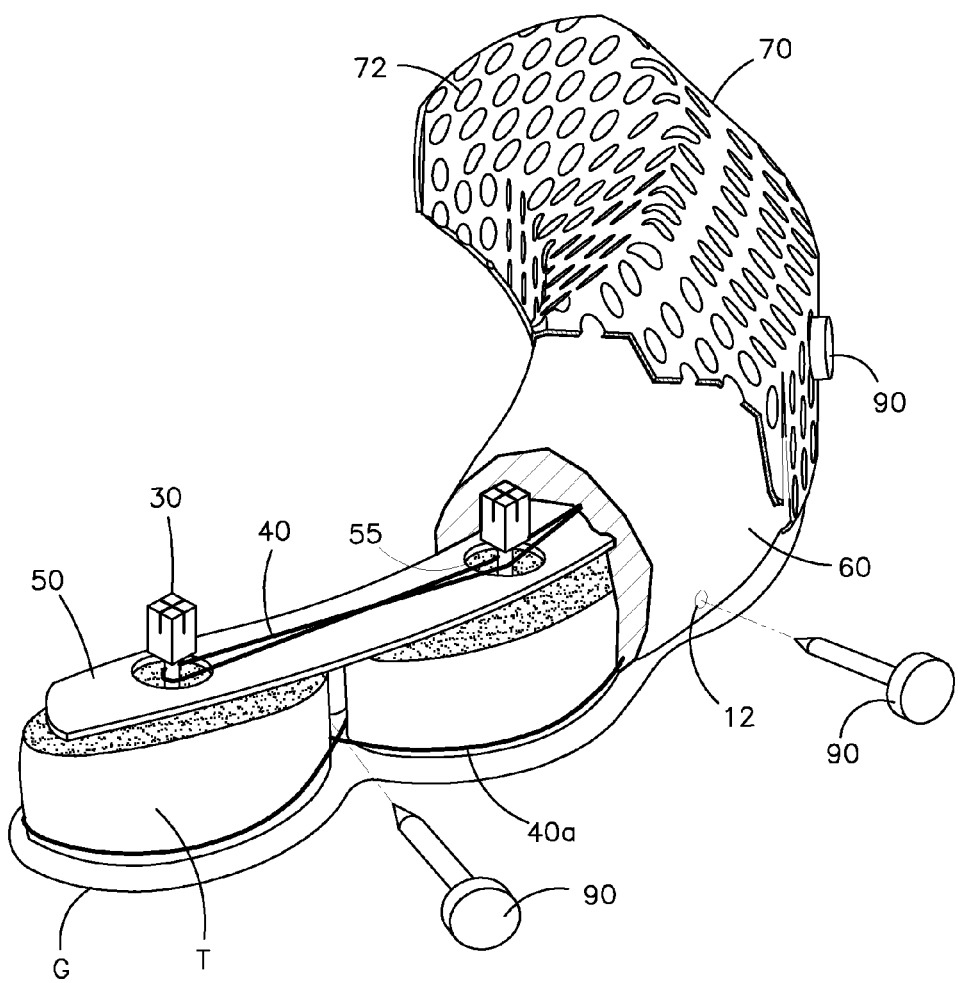
FIG. 5 is an isometric view of the incisors of a cow with partially cut bonding agent and overdenture.

Referring now to the drawings, where the present invention is generally referred to with numeral 10, it can be observed that it basically includes a metallic infrastructure rigidly mounted to the bovine's incisors, as a group, to prevent relative movement, and a malleable metallic overdenture 70 to replace the original teeth's function. Dental prosthesis 10 includes the use of self-tapping fastening members 30 mounted to the animal's teeth T, at an off-centered location away from the central teeth nerves N towards the inner side of the incisors, surgical wire 40 and support plate 50, bonding agent 60 and overdenture 70, as best seen in FIG. 1. In one of the embodiments, members 30 include a headed end 32 with a small portion of the shank 34 exposed, as seen in FIG. 1. Optionally, wire 40a is passed between adjacent teeth to prevent their relative movement. Preferably, wire 40a follows an 8-shape path, as seen in FIGS. 1A through 1C. Surgical steel wire 40 is passed between adjacent fastening members 30, mostly with 8-shape turns, to hold the teeth T as a group using the exposed shank 34 to tie them together, as best seen in FIGS. 2 through 2C. Wire 40 is kept above gum G to avoid lacerations. The different elements that are sequentially mounted are shown in FIG. 3. Support plate 50 is then affixed to incisor teeth T and members 30 pass through openings 52. Plate 50 ensures that relative movement of individual teeth is prevented. A dental bonding agent, resin or cement 60 is applied to the metallic infrastructure and exposed upper surface of teeth T, as seen in FIG. 4. A malleable metal overdenture 70 with through openings or holes 72 is mounted over the incisors and metallic infrastructure, covering them. As pressure is applied, agent 60 roughly conforms to the metallic infrastructure and incisor teeth T, permitting some of bonding agent 60 to extrude out through holes 72 producing further grip. Bendable flaps 74 at the ends of overdenture 70 wrap around the outer ends of the last teeth T. Retention fastening members 80 are mounted transversally to keep overdenture 20 in place, as best seen in FIGS. 4 and 5. Members 80 pass through holes or spaces 72 of overdenture 70.

The present method for affixing a crown or prosthesis in bovine animals includes the steps of:

A) Restraining the animal, particularly its jaw, to allow a user to undertake the dental work.

B) Drilling one hole in each of the animal's incisors, away from the center where nerve N is located, as shown in FIG. 1. Preferably, the hole is off-centered towards the inner side of incisor teeth T.

C) Screwing in self-tapping anchorage fastening members 30, substantially parallel to each other and substantially perpendicular to the worn out teeth plane.

D) Tying with surgical steel wire 40a teeth T with those screw members 30 of adjacent teeth T to prevent their individual relative movement. One way of tying the incisors is by passing the wire forming an 8-shape configuration with at least one pass around each incisor.

E) Mounting support plate 50 adjacent to the teeth T and substantially conforming to the worn out teeth plane. Fastening members 30 pass through through holes 55 of support plate 50. Wire 40 is used to tie members 30 and keep plate 50 in place. Wire 40 is passed between members 30 defining 8-shape configurations.

F) Applying a sufficient amount of a dental bonding agent to the resulting infrastructure consisting of members 30, wire 40 and plate 50. One of the preferred ways for applying boarding agent 75 is to use overdenture 70 as described below.

G) Mounting a malleable metallic overdenture 70 with through holes 72 over the infrastructure and teeth. Overdenture 70 is preferably filled with bonding agent 60 in its concave side. Applying force to permit the bonding agent to fill the entire concave side of overdenture 70 be extruded through the through holes 72. The overdenture includes two flaps 74 at its ends to embrace and conform to the last incisors.

H) Retention fastening members in between 90 are mounted transversally through the metallic overdenture 70 and in between the animal's teeth from the outer side. These members 90 can be implemented with elongated pins.

The present method is trauma-free and extends the life of the cattle by allowing it to continue feeding itself for years. The animal starts feeding itself immediately after the procedure is completed and the animal is released.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for mounting a prosthesis in cattle with worn out incisors that includes the steps of:

A) restraining the animal, particularly its jaw, to allow a user to undertake the dental work;

B) drilling one hole in each of the animal's worn out incisors, away from the center where the central nerve is located and towards the inner side of the incisors;

C) screwing in self-tapping anchorage fastening members 30 in said holes, keeping fastening members substantially parallel to each other and substantially perpendicular to the incisors worn out plane;

D) tying with surgical steel wire each individual incisor with adjacent incisors to prevent their individual relative movement;

E) mounting support plate 50 adjacent to and substantially following the worn out teeth plane said plate having through holes that permit members 30 to pass through and protruding a predetermined distance and tying with surgical with surgical steel wire each individual protruding fastening member resulting in a unitary metallic infrastructure;

F) applying a sufficient amount of a dental bonding agent to the resulting infrastructure consisting of members 30, wire 40 and plate 50;

G) mounting a malleable metallic overdenture 70 with through holes 72 over the infrastructure and teeth, applying sufficient force to permit the bonding agent to be extruded through the through holes, the overdenture includes a concave side that substantially conforms to and covers said incisors and further includes two ends with flaps 74; and H) mounting retention fastening pins transversally through the metallic overdenture and between the animal's incisors to further secure the engagement of said overdenture to said bonding agent.

* * * * *